US012642474B2

(12) United States Patent
Prisco et al.

(10) Patent No.: US 12,642,474 B2
(45) Date of Patent: Jun. 2, 2026

(54) COMPUTATIONAL METHOD FOR LOCALIZING THE ORIGIN OF ARRHYTHMIA

(71) Applicant: Regents of the Univeristy of Minnesota, Minneapolis, MN (US)

(72) Inventors: Anthony Robert Prisco, Minneapolis, MN (US); Venkatakrishna Tholakanahalli, Minneapolis, MN (US); Matthew Olson, Minneapolis, MN (US)

(73) Assignees: REGENTS OF THE UNIVERSITY OF MINNESOTA, Minneapolis, MN (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 325 days.

(21) Appl. No.: 18/290,643

(22) PCT Filed: Jul. 20, 2022

(86) PCT No.: PCT/US2022/037711
§ 371 (c)(1),
(2) Date: Jan. 19, 2024

(87) PCT Pub. No.: WO2023/003953
PCT Pub. Date: Jan. 26, 2023

(65) Prior Publication Data
US 2024/0260883 A1 Aug. 8, 2024

Related U.S. Application Data

(60) Provisional application No. 63/203,366, filed on Jul. 20, 2021.

(51) Int. Cl.
*A61B 5/363* (2021.01)
*A61B 5/00* (2006.01)
(Continued)

(52) U.S. Cl.
CPC .............. *A61B 5/363* (2021.01); *A61B 5/271* (2021.01); *A61B 5/283* (2021.01); *A61B 5/339* (2021.01);
(Continued)

(58) Field of Classification Search
None
See application file for complete search history.

(56) References Cited

U.S. PATENT DOCUMENTS

| | | | |
|---|---|---|---|
| 2013/0158615 A1* | 6/2013 | Mahajan | ............ A61N 1/39622 |
| | | | 607/14 |
| 2014/0107510 A1* | 4/2014 | Bogun | ................... A61B 5/316 |
| | | | 600/523 |

(Continued)

OTHER PUBLICATIONS

International Preliminary Report on Patentability corresponding to PCT/US2022/037711 dated Jan. 18, 2024.
(Continued)

*Primary Examiner* — Michael W Kahelin
(74) *Attorney, Agent, or Firm* — Husch Blackwell LLC

(57) ABSTRACT

A system for VT localization comprises an electrocardiograph (ECG) device for detecting electrical signals of a ventricular fibrillation event in a patient and producing ECG data, a localizer, and a display device. The localizer comprises a memory and a processor, the memory storing a model and one or more parameters of the model. The memory further stores instructions that when executed by the processor cause the processor to receive the ECG data, and generate a determination indicating whether a detected VT signal arose from an endocardial surface or epicardial surface based on signal averaged waveform for each of the
(Continued)

200

Receive 12-Lead ECG
202

Average individual beats to generate signal averaged waveform
204

Determine the start of a VT signal
206

Calculate initial rate of change (dV/dt)
208

Determine if arrhythmia of patient arose from epicardial or endocardial surface
210

Display the determination
212 leads. The display device is configured to output the determination, which can also be communicated to follow-on provider systems.

20 Claims, 8 Drawing Sheets

(51) Int. Cl.
| | | |
|---|---|---|
| *A61B 5/271* | (2021.01) | |
| *A61B 5/283* | (2021.01) | |
| *A61B 5/339* | (2021.01) | |
| *A61B 5/367* | (2021.01) | |

(52) U.S. Cl.
CPC .............. *A61B 5/367* (2021.01); *A61B 5/686* (2013.01); *A61B 2562/222* (2013.01)

(56) References Cited

U.S. PATENT DOCUMENTS

| | | | | |
|---|---|---|---|---|
| 2018/0235493 A1 | 8/2018 | Zhang | | |
| 2019/0090774 A1* | 3/2019 | Yang | ..................... | G16H 50/50 |

OTHER PUBLICATIONS

International Search Report corresponding to PCT/US2022/037711 dated Sep. 29, 2022.
International Written Opinion corresponding to PCT/US2022/03711 dated Sep. 29, 2022.

\* cited by examiner

Fast
conduction

Slow
conduction

200

Receive 12-Lead ECG
202

Average individual beats to generate signal
averaged waveform
204

Determine the start of a VT signal
206

Calculate initial rate of change (dV/dt)
208

Determine if arrhythmia of patient arose from
epicardial or endocardial surface
210

Display the determination
212

Average individual beats to calculate signal averaged waveform

Repeat on all leads

Lead I     Lead aVR     Lead V1     Lead V4

Lead II     Lead aVL     Lead V2     Lead V5

Calculate:
1. Initial (first 30 ms) rate of change (dV/dt)

2. Average rate of change (from start of depolarization to max deflection from baseline)

Lead III     Lead aVF     Lead V3     Lead V6

COMPUTATIONAL METHOD FOR LOCALIZING THE ORIGIN OF ARRHYTHMIA

CROSS-REFERENCE TO RELATED APPLICATION

This application is a U.S. National Phase of International Application No. PCT/US2022/037711, filed Jul. 20, 2022, which claims priority from U.S. Provisional Application Ser. No. 62/203,366 filed on Jul. 20, 2022, the disclosures of which are hereby incorporated by reference in its entirety.

FEDERALLY SPONSORED RESEARCH

This inventions disclosed herein were made with U.S. government support under HL144472 awarded by the National Institutes of Health. The U.S. government may have certain rights in the invention.

TECHNICAL FIELD

Embodiments of the present disclosure relate generally to the field of cardiovascular medicine and more particularly to systems and methods for mapping and classifying endocardial versus epicardial ventricular tachycardia.

BACKGROUND

Ventricular tachycardia (VT) is a life-threatening cardiac arrhythmia that if not terminated via defibrillation (electric shock), will lead to sudden cardiac death. To prevent sudden cardiac death in this patient population, an implantable defibrillator can be implanted that will deliver a shock to the patient to terminate the arrhythmia after it is detected. However, this therapy only terminates the arrhythmia preventing death; it does nothing to prevent future events.

Definitive therapy requires the origin or critical path of the arrhythmia to be identified in the heart. Once this is done it can be eliminated through radiofrequency ablation. To accomplish this, a cardiologist who is specialized in arrhythmias performs an invasive procedure called an electrophysiological study where the origin of the arrhythmia is "mapped," and this area is then ablated (burned using radiofrequency energy). This process can take up to several hours. Most of the time is spent identifying the origin or the critical path of the arrhythmia.

An important part in ablating an arrhythmia relies on creating a 3D map of the location of the arrhythmia. From this map, a portion of the patient's heart is targeted through radiofrequency ablation. Arrhythmias that arise from the inside of the heart (endocardial) are accessed by inserting several catheters in the patient's leg vessels. Arrhythmias that arise from the outside of the heart (epicardial) are accessed via needle access beneath the breastbone into the sac around the heart or through surgical approach.

Unfortunately, these two approaches require significantly different equipment and expertise. For example, epicardial arrhythmias may require an electrophysiologist who has expertise in accessing epicardial space or a cardiac surgeon who can perform invasive surgery to access the space around the heart. Typically, endocardial mapping is attempted first (through the leg vessels) as it is less invasive. However, this conventional approach is still invasive and time intensive. Another conventional approach is to derive morphological characteristics from the standard 12-lead electrocardiogram (ECG) criteria that can be used to predict whether a VT is epicardial in origin. Unfortunately, for many of these criteria, when scaled to clinical practice the generalizability is unsuccessful due to anatomical location of the VT and slow myocardial conduction.

Consequently, there remains a need for systems and methods for quickly distinguishing between endocardial and epicardial arrhythmias in a noninvasive and accurate manner.

SUMMARY

Embodiments of the present disclosure provide systems and methods for non-invasively distinguishing between endocardial and epicardial arrhythmias. Such embodiments can identify and target a critical site of the arrhythmia to decrease the time of the procedure and increase the likelihood of this success.

In a first aspect of the present disclosure, a system for ventricular tachycardia (VT) localization comprises a localizer comprising a memory and a processor. The memory can store instructions that when executed by the processor cause the processor to receive electrocardiograph (ECG) data from an ECG device, the ECG data including electrical signals of consecutive beats of VT in a patient as recorded through each of a plurality of leads, and make a determination regarding whether the VT arises from the endocardial surface of the epicardial surface. An output device can be communicatively coupled to the localizer and configured to output the determination.

In embodiments, the localizer can generate a signal averaged waveform for each lead of the plurality of leads from the ECG data, the signal averaged waveform representing single beat, calculate a depolarization rate for a time period for each of the signal averaged waveforms, and calculate a combined depolarization rate based on the depolarization rate of at least two of the signal averaged waveforms. In response to the combined depolarization rate being above a threshold, the localizer can generate a determination that the VT arises from an endocardial surface of the heart of the patient. In response to the combined depolarization rate not being above the threshold, generate a determination that the VT arises from the epicardial surface of the heart of the patient. In embodiments, the localizer can generate a determination that the location of the VT is inconclusive when the combined depolarization rate is below a second threshold.

In embodiments, the ECG data includes at least 10 consecutive beats of VT in the patient. In embodiments, the threshold can be 6 mV/s.

In embodiments, wherein the time period is the initial 30 ms of depolarization. In embodiments, the time period is a maximum deflection period extending from the beginning of depolarization to the time of maximum deflection from baseline.

In embodiments, the determination can be based on the waveforms of all leads of a 12 lead ECG, only the limb leads, only the precordial leads, or any other combination. In an embodiment, the plurality of leads includes limb leads and the combined depolarization rate is calculated based on the depolarization rate of the signal averaged waveform of a I lead, a II lead, a III lead, an aVR lead, an aVL lead, and aVF lead. In an embodiment, the plurality of leads includes precordial leads and the combined depolarization rate is calculated based on the depolarization rate of the signal averaged waveform of each of a V1 lead, a V2 lead, a V3 lead, a V4 lead, and a V5 lead. In an embodiment, the ECG device is as 12-lead ECG device, and the combined depolarization rate is calculated based on the depolarization rate of each of the twelve leads.

In embodiments, the output device comprises a display configured to present the determination to a user. The user can perform a procedure to treat the VT based on the determination. In embodiments, the output device comprises a network interface configured to communicate the determination to an auxiliary computing device. In embodiments, the system can be a component of an implantable cardiac device.

In a second aspect of the present disclosure, a computer-implemented method for localizing ventricular tachycardia (VT) within the heart of a patient includes receiving, by localizer comprising a memory and a processor, electrocardiograph (ECG) data from an ECG device, the ECG data including electrical signals of consecutive beats of VT in the patient as recorded through each of a plurality of leads, generating a signal averaged waveform for each lead of the plurality of leads from the ECG data, the signal averaged waveform representing single beat, calculating a depolarization rate for a time period for each of the signal averaged waveforms, and calculating a combined depolarization rate based on the depolarization rate of at least two of the signal averaged waveforms. In response to the combined depolarization rate being above a threshold, the method can include generating a determination that the VT arises from an endocardial surface of the heart of the patient; and in response to the combined depolarization rate not being above the threshold, the method can include generating a determination that the VT arises from the epicardial surface of the heart of the patient.

In embodiments, the method further comprising procedure on the patient to treat epicardial VT when the determination is that the VT arises from the epicardial surface or to treat endocardial VT when the determination is that the VT arises from the endocardial surface.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures.

Figure 1:
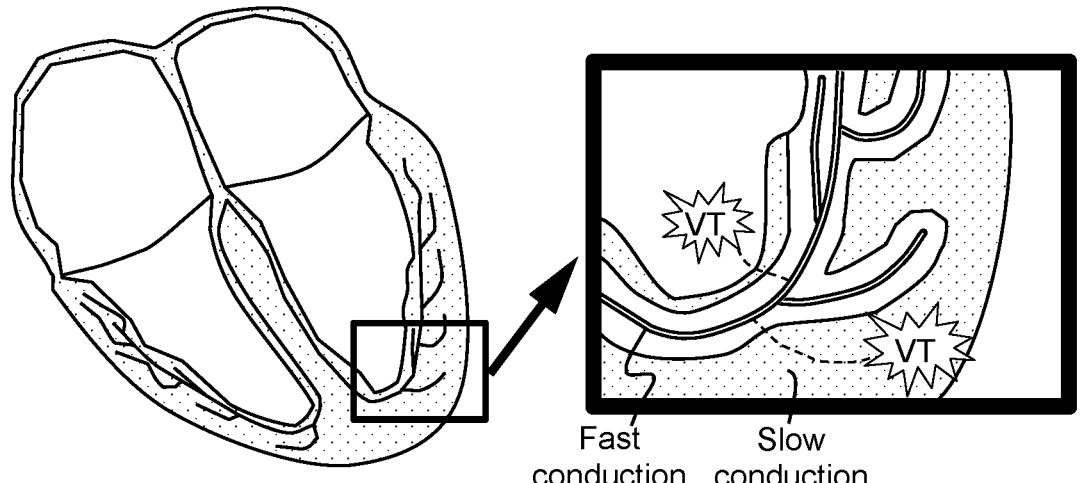
FIG. 1 is a diagram schematically depicting the His-Purkinje system of a heart.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 2:
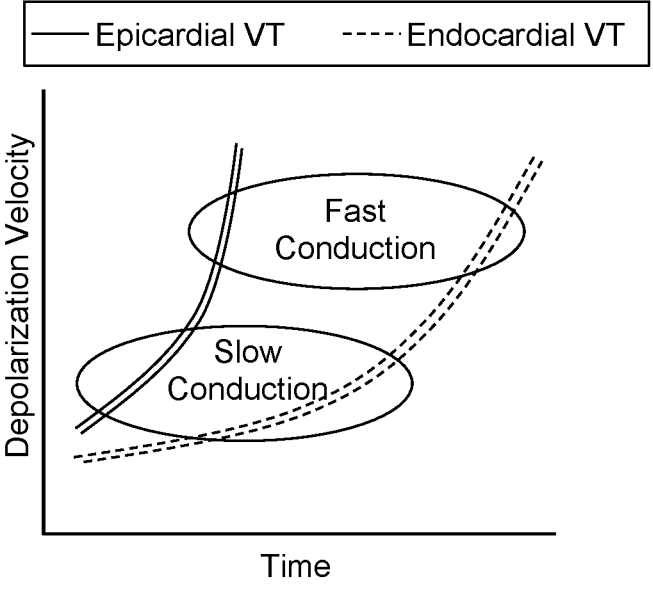
FIG. 2 is a graph depicting the general depolarization velocity over time of an epicardial VT and an endocardial VT, as may be analyzed by embodiments.

Embodiments of present disclosure use a standard 12-lead ECG to predict whether a VT arose from an endocardial surface or epicardial surface. The embodiments leverage the fact that the His-Purkinje system, depicted in FIG. 1, is an endocardial structure. Because conduction through neural tissue (His-Purkinje system) is faster than through muscle tissue (myocardium), VTs arising or involving endocardial exit invokes the His-Purkinje system more readily as compared to epicardial VTs which need to first traverse through the myocardium prior to depolarizing the His-Purkinje system. FIG. 2 is a graph of the depolarization velocity over time of an epicardial VT and an endocardial VT. Based upon these anatomical characteristics, initial depolarization of an epicardial VT will be slower when compared to an endocardial VT as depicted in FIG. 2.

Figure 3:
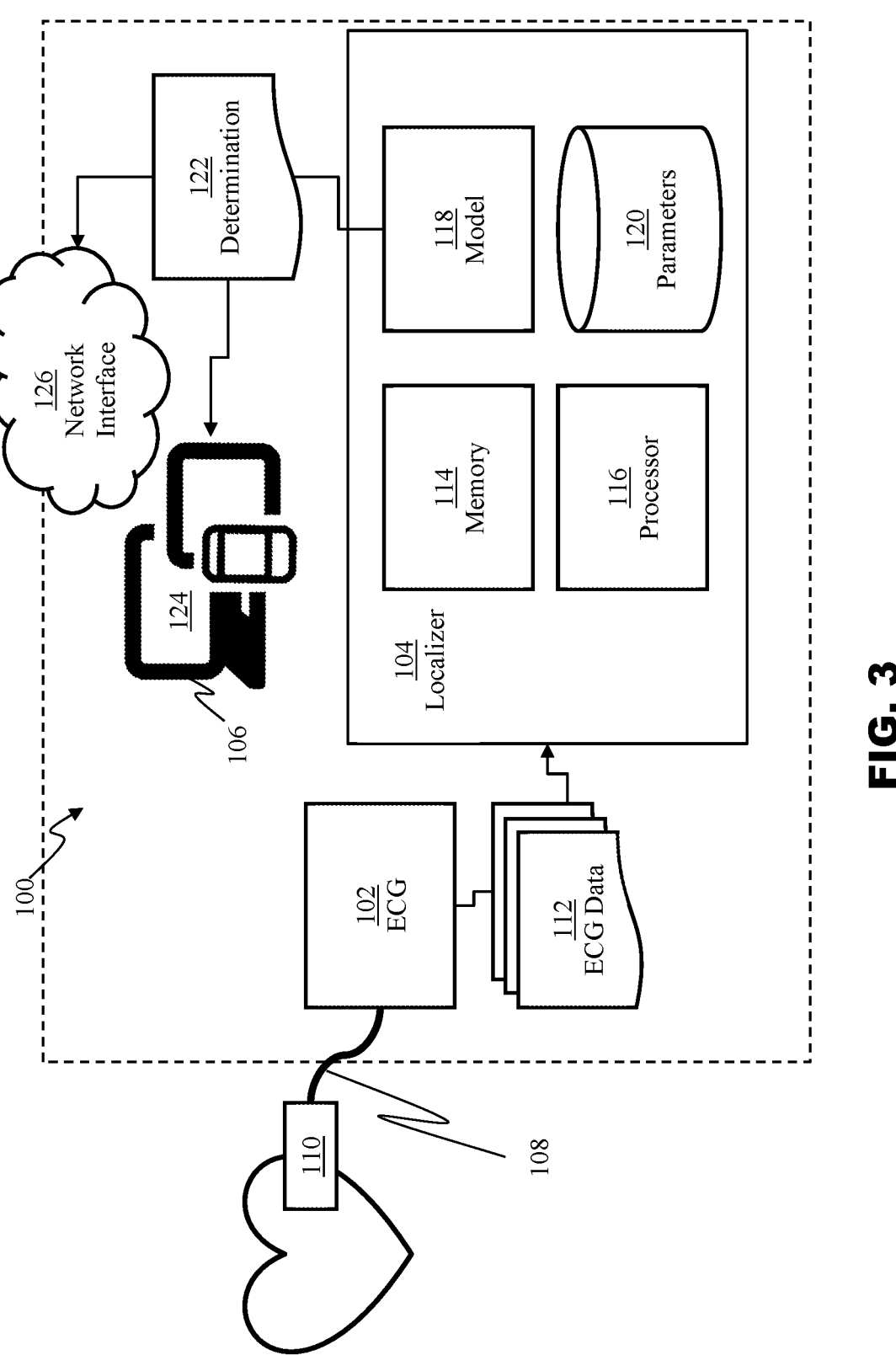
FIG. 3 is a schematic diagram depicting a system for VT localization, according to an embodiment.

FIG. 3 is a schematic diagram depicting system 100 for VT localization, according to an embodiment. System 100 can comprise an electrocardiogram (ECG) sensor 102, localizer 104, and display device 106.

ECG sensor 102 can comprise one or more leads 108. Each lead 108 can comprise one or more electrodes 110 for placement proximate the body of a patient. Each lead 108 can further comprise electrically conductive, insulated wires, for transmitting electrical energy from electrodes 110 to ECG sensor 102. In an embodiment, ECG sensor 102 comprises 12 leads 108 each with two electrodes 110. In other embodiments, more or fewer leads 108 with more or fewer electrodes can be used. Each lead 108 can be unipolar (single electrode), bipolar (two electrode), or include other numbers of electrodes.

ECG sensor 102 can comprise a voltmeter or other component for measuring the electrical signal between electrodes 110 of leads 108. Embodiments can measure one or more aspects of the electrical signal such as voltage, current, capacitance, and the like. ECG sensor 102 can transmit recorded signals to localizer 104 as ECG data 112.

ECG data 112 can comprise raw signal data, such as streams of binary or text data representing discrete measurements of electrical activity. In other embodiments, ECG data 112 can comprise waveform data in an image format, or one or more standard ECG waveform data formats such as Health Level Seven (HL7) Annotated ECG Waveform Data Standard (aECG), Mortara XML (E-Scribe & H-Scribe), GE MUSE XML (Transactional XML), Philips XML (Sierra XML), Schiller XML, AMPS binary ECG, ISHNE, SCP, and/or MIT.

Figure 6:
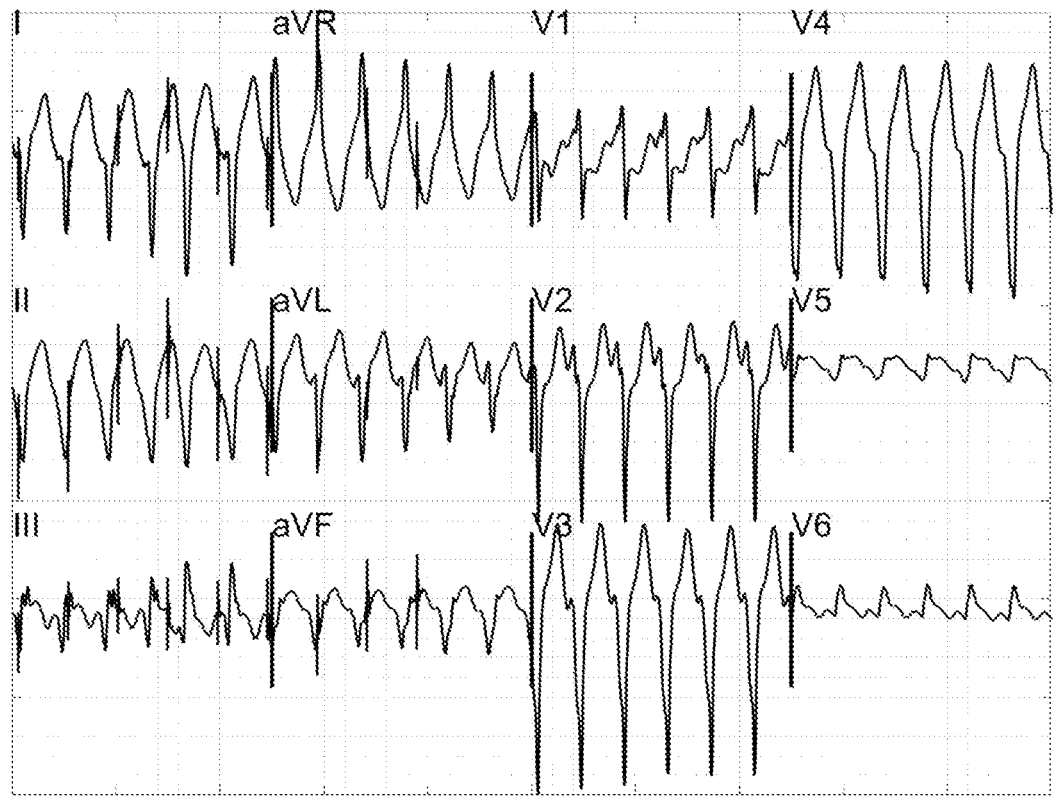
FIG. 6 is an example of a 12-lead ECG graph as may be analyzed by embodiments.

In embodiments, ECG data 112 can comprise a 12-Lead ECG, such as the exemplary 12-Lead ECG indicative of a VT rhythm depicted in FIG. 6. 12-Lead ECGs are non-invasive and can be obtained by emergency departments, outpatient clinics, and inpatient wards. In embodiments, a 12-Lead ECG including at least 10 consecutive beats is preferred in order to account for dissociated atrial activity. The collected VT signals can be averaged to calculate a representative waveform and a rate of depolarization (dV/dT). This process can be completed for each of the 12 surface leads both for the initial 30 milliseconds, and from the start of the VT until the point of maximal deflection. The start of the VT signal can then be determined and the change in voltage calculated for each lead both from the initial 30 milliseconds and until the maximum deflection index.

Localizer 104 can comprise a computing device including a memory 114 and a processor 116. Memory 114 can provide storage for one or more VT localization models (referred to herein as model 118) and associated parameters 120. Model 118 can receive ECG data 112 and produce determination 122. Model 118 can comprise a localization algorithm that can be trained, by iterative modification of parameters 120 to recognize signals that are indicative of an endocardial VT or an epicardial VT. In embodiments, memory 114 can provide storage for one or more machine learning algorithms or models and associated parameters 120.

Determination 122 can be an indication of whether ECG data 112 represents signals indicative of an endocardial VT or an epicardial VT. Determination 122 can also include an indication the result was inconclusive. In yet other embodiments, determination 122 can include a likelihood (such as a decimal or percentage chance) that ECG data 112 represents a VT and a likelihood that the VT is endocardial or epicardial.

Display device 106 is communicatively coupled to localizer 104 to receive and output determination 122 to the user. Display device 106 can comprise a visual display, such as a computer screen or monitor, a digital readout device, light or dial indicators, or the like. Display device 106 can comprise an audio output, such as speakers or headphones. In embodiments, display device 106 can comprise a computing device including user interface 124.

User interface 124 can receive user inputs and provide user outputs regarding configuration of system 100. User interface 124 can comprise a mobile application, web-based application, or any other executable application framework. User interface 124 can reside on, be presented on, or be accessed by any computing devices capable of communicating with the various components of system 100, receiving user input, and presenting output to the user. In embodiments, user interface 124 can reside or be presented on a smartphone, a tablet computer, laptop computer, or desktop computer.

In embodiments, display device 106 can comprise, or be communicatively connected to network interface 126. Determination 122 can be transmitted via network interface 126 to one or more remote computing systems. In embodiments, network interface 126 can enable system 100 to be communicatively coupled to one or more patient care management systems. For example, determination 122 can be transmitted from an emergency response location, where system 100 is receiving ECG data 112 to a catheterization laboratory, such that users can prepare for arrival of a patient for catheter-based procedures to provide definitive treatment for either an endocardial VT or an epicardial VT.

Figure 4:
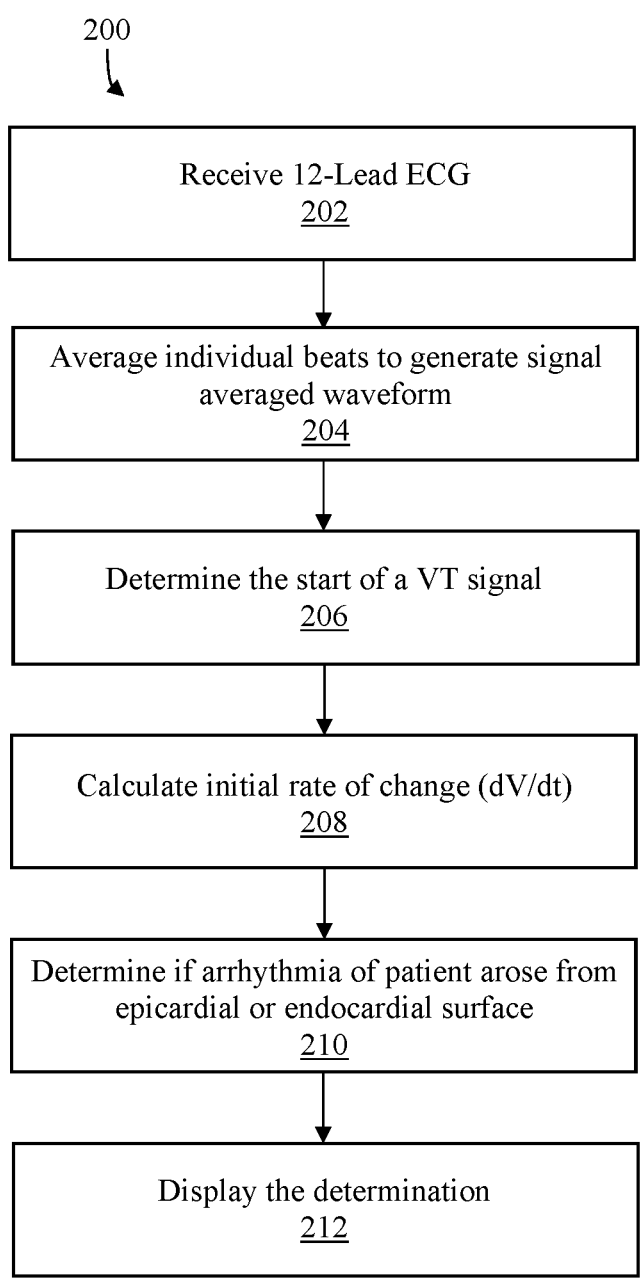
FIG. 4 is a flowchart depicting a method for VT localization, according to an embodiment.

FIG. 4 is a flowchart depicting method 200 for determining if a VT signal is endocardial or epicardial. At 202, an ECG of a patient is received. In embodiments, the ECG is a 12-lead ECG. In other embodiments, a varying number of leads can be used. At 204, individual beats of the 12-Lead ECG are averaged to generate an averaged waveform for each lead. At 206, the start of each VT signal is determined based on deflections of the signal. At 208, the initial rate of change is calculated for each VT signal. In embodiments, the initial rate of change is calculated for the first 30 ms of each lead. At step 210, a determination can be made based on the averaged waveform and the initial rate of change that the patient's arrhythmia arose from the epicardial surface or endocardial surface. At 212, the determination can be output to a display device, such as display device 106.

Embodiments of the present disclosure can generate a signal averaged waveform of a standard 12-Lead ECG of a patient to determine if a VT signal is endocardial or epicardial. Such a determination is precise, non-invasive, and greatly reduces the amount of time required to identify the origin or the critical path of the arrhythmia. Embodiments can enable selection of appropriate treatments for the arrhythmia via radiofrequency ablation. Selected treatments can then be used to identify which professionals (e.g. cardiologists or electrophysiologists) should be present. Embodiments of the present disclosure represent an improvement over conventional approaches, including endocardial mapping requiring inserting several catheters in the leg vessels of a patient.

Figure 5:
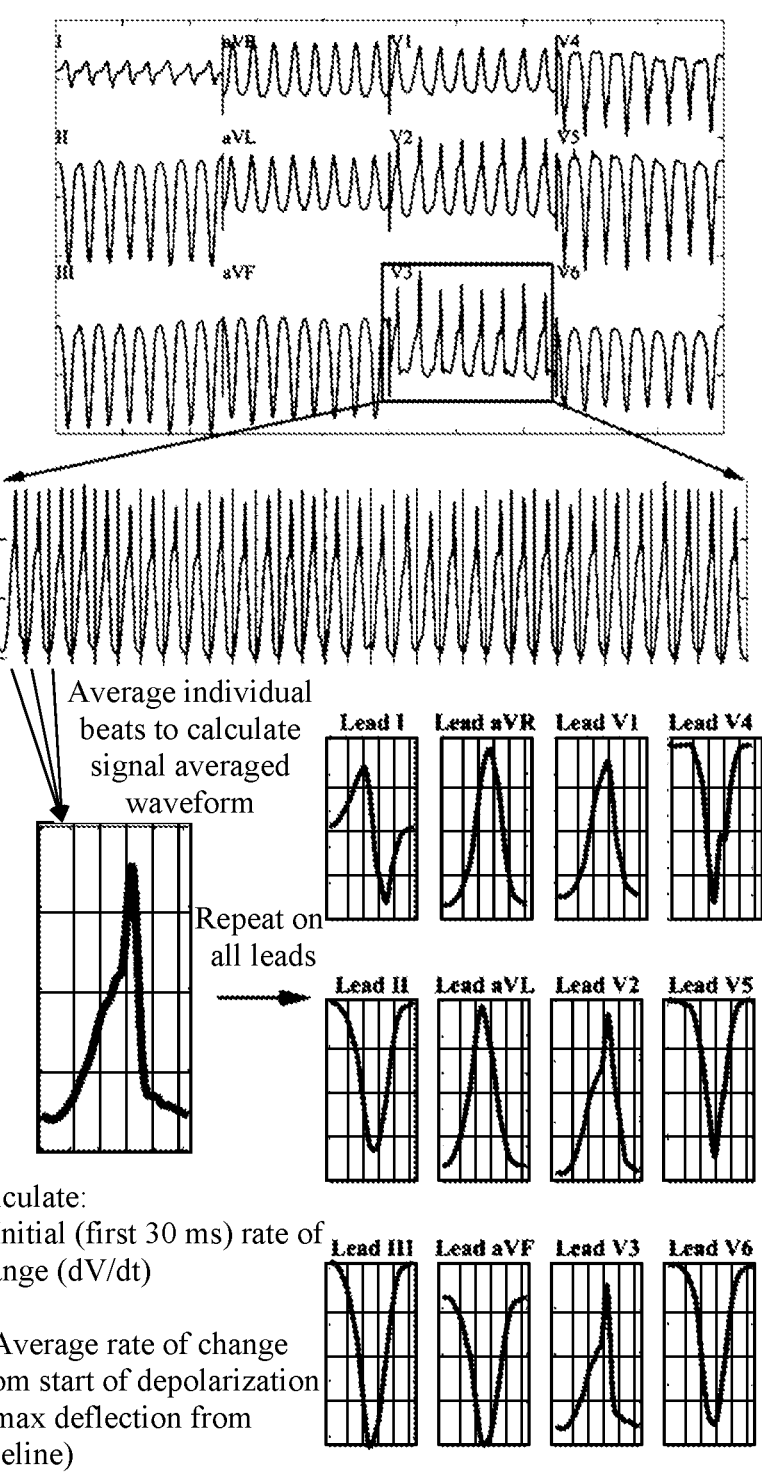
FIG. 5 is a series of graphs depicting a method for VT localization, according to an embodiment.

FIG. 5 depicts a process, similar to method 200, for generating a representative waveform for exemplary simultaneous recordings of 12 standard ECG leads according to an embodiment.

FIG. 6 is an exemplary 12-lead ECG that can be obtained clinically by emergency departments, outpatient clinics, and inpatient wards. The 12-Lead ECG can include 10 seconds of collected VT that can be averaged to calculate a representative waveform and a rate of change of depolarization (dV/dT). The use of a signal averaged waveform reduces noise between each beat.

The application of signal averaging activity can provide noise reduction benefits which can be particularly beneficial because every VT beat is slightly different due to atrial activity. If not reduced, noise present in the signal could be amplified by calculation of slopes (such as rates of depolarization) in the signal. A signal averaged waveform is a signal processing technique designed to increase the signal-to-noise ratio of a periodic signal by decreasing random variations in the repeating signal. Any signal-averaging technique applicable to electrocardiogram data known in the art can be used in various embodiments.

Figure 7:
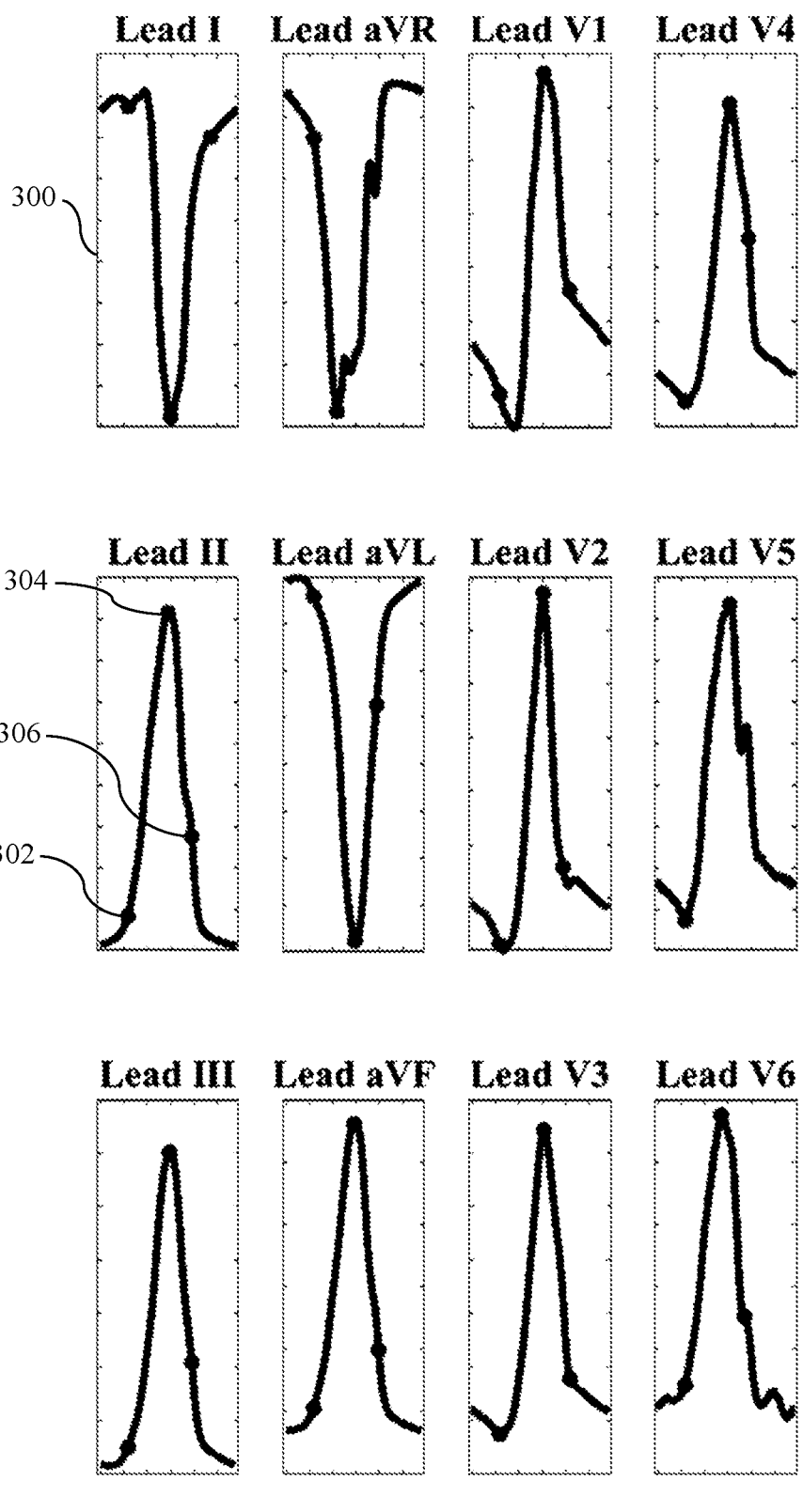
FIG. 7 is a series of representative depolarization graphs for each lead from the exemplary 12-lead ECG of FIG. 6.

FIG. 7 depicts each individual recording from FIG. 6 signal-averaged to generate representative depolarization 300 for each lead. The start deflection 302, end deflection 304, and maximum deflection 306 of the signal are marked. The representative depolarizations 300 are used to calculate the initial rate of change for the first 30 ms of each lead. The initial rate of change for each lead can then be used to determine if a patient's arrhythmia arose from the endocardial surface or epicardial surface. This determination can be accomplished due to the differences between endocardial and epicardial depolarization rates.

From the signal averaged waveform, the start of the VT ($VT_i$) can be identified and independently validated by cardiac electrophysiologists. In each of the twelve signal-averaged leads, the maximum deflection index (MDI) is calculated by determining the furthest point from the average of the signal ($VT_{max}$). From $VT_i$ and $VT_{max}$ two calculations are made that are analogous to the relative "speed" of the depolarization including: depolarization from the first 30 ms of the beat ($dV_{initial}/dt$), and depolarization from the start of the beat to the MDI ($dV_{average}/dt$). These two parameters can be calculated as follows:

$$\frac{dV_{initial}}{dt} = \frac{|VT_i - VT_{i+30\,ms}|}{30\,ms}$$

Where $VT_i$ is the signal voltage at the beginning of the signal averaged beat, and $VT_{i+30\,ms}$ is the voltage following 30 milliseconds. The averaged signal of the depolarization is calculated as follows:

$$\frac{dV_{average}}{dt} = \frac{||VT_i - VT_{max}|||}{Ti_{max}}$$

Where $VT_i$ is the signal voltage at the beginning of the signal averaged beat and $T_i$ is the time at which the depolarization starts, $VT_{max}$ is the voltage at the maximum deflection index, $T_{max}$ is the time at maximum deflection index.

From these calculations, embodiments can identify if an arrhythmia arises from the inside or outside of the heart prior to performing an invasive study. This identification is possible because the initial rate of depolarization of the heart is faster in patients with endocardial versus epicardial VT. In embodiments, a threshold parameter can be set for which values of dV/dt are indicative of endocardial versus epicardial VT. In embodiments, readings less than 6 mV/s are considered high sensitivity for endocardial VT. In embodiments, the threshold parameter can be configurable based on desired sensitivity and specificity.

Embodiments can incorporate on or more machine learning feedback or training mechanisms. For example, model epicardial. Embodiments identify patients who have epicardial VT or endocardial VT, and thereby improve patient outcomes by automatically alerting a cardiac catheterization laboratory what staff and equipment are necessary to provide definitive treatment.

Embodiments of the present disclosure can comprise, or be incorporated as software within, an electrophysiology (EP) mapping or recording system to analyze and plan as to whether epicardial access is necessary. Embodiments can be incorporated into standard 12-lead ECG software analysis systems to provide an initial prediction of the origin of a VT exit (epicardial vs. endocardial). Embodiments provide non-invasive analysis that can be done prior to an invasive study to plan for epicardial ablation.

In a retrospective study including with non-ischemic VT, successful elimination of the arrhythmia following the procedure with ablation of the site of epicardial exit sites, EP studies were then retrospectively analyzed, and runs of at least ten consecutive beats of VT were exported for analysis. Runs of VT that were extracted for analysis were obtained prior to any ablation being performed.

From each of the 12 leads, $dV_{initial}/dt$ and $dV_{average}/dt$ were calculated. Within each single subject, the 12 leads were consolidated through three different averages: all twelve leads ($dV_{all}/dt$), limb (I, II, II, aVR, aVL, aVF) leads ($dV_{limb}/dt$) and the precordial (V1-V6) leads ($dV_{precordial}/dt$) Both $dV_{initial}/dt$ and $dV_{average}/dt$ were compared between endocardial and epicardial VTs using a Wilcoxon rank sum test to compare for statistical significance, as presented in Table 1 below.

TABLE 1

| | All Leads | | Limb Leads | | Precordial Leads | |
|---|---|---|---|---|---|---|
| | Average | Initial | Average | Initial | Average | Initial |
| Endocardial | $11.4 \pm 3.7$ | $9.9 \pm 4.8$ | $9.7 \pm 4.4$ | $8.4 \pm 5.4$ | $13.2 \pm 8.5$ | $11.3 \pm 7.8$ |
| Epicardial | $6.3 \pm 3.1$ | $4.6 \pm 2.2$ | $4.8 \pm 3.5$ | $3.2 \pm 1.7$ | $8.5 \pm 6.0$ | $6.2 \pm 3.2$ |
| P-Value | 0.0353 | 0.0299 | 0.0001 | 0.0246 | 0.2952 | 0.3996 |

118 with one or more sets of training data. Each set of training data can include ECG data, and a label indicating whether the actual location of the VT was on the epicardial or endocardial surface. Model 118 can select or modify an initial threshold data based on the calculated rate of depolarization and the label for each set of training data. As such, model 118 can automatically update parameters 120 such as the threshold used to determine epicardial or endocardial based on provided feedback.

Figure 8:
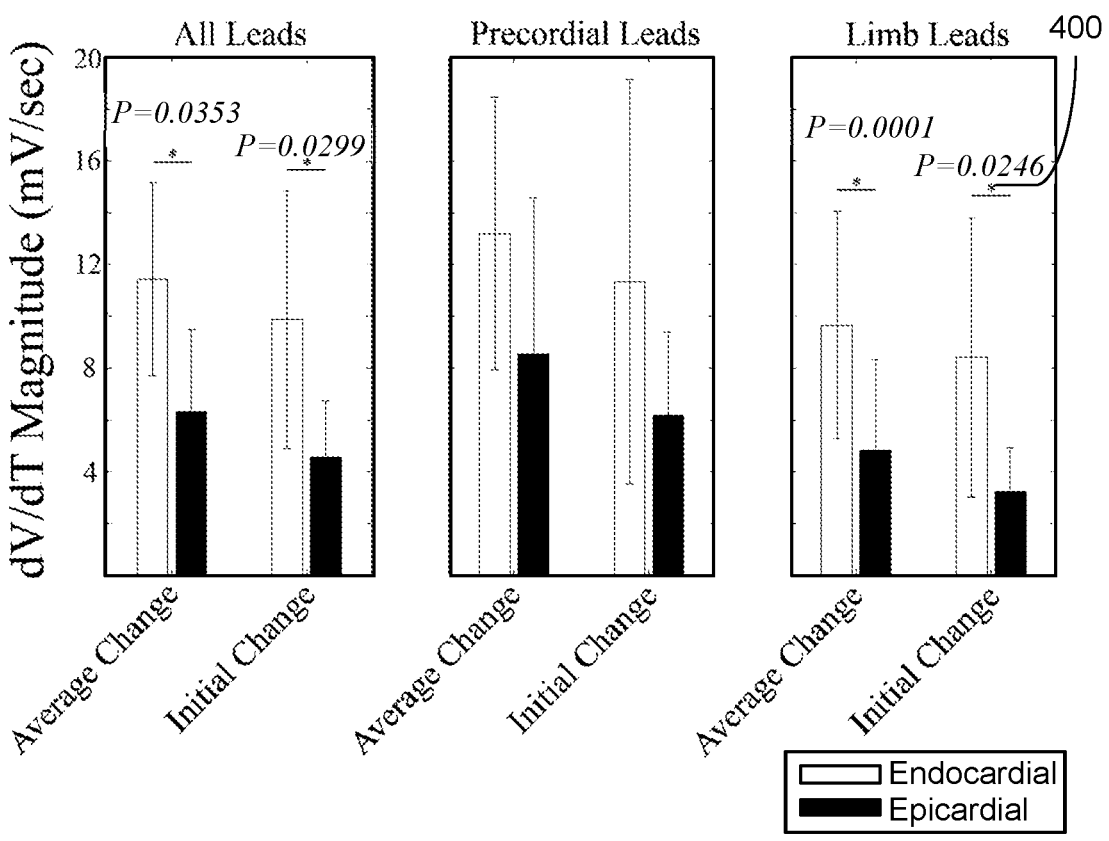
FIG. 8 is a series of graphs indicating the comparison rate of change in depolarization between epicardial and endocardial VT for an exemplary patient.

FIG. 8 depicts a comparison between endocardial and epicardial depolarization rates for an exemplary patient. The initial and average depolarization rates are calculated and averaged within a patient (all twelve leads, precordial, or limb leads averaged) and compared between epicardial and endocardial arrhythmias. Asterisks 400 indicate statistical significance between groups, with a p-value less than 0.05.

Figure 9:
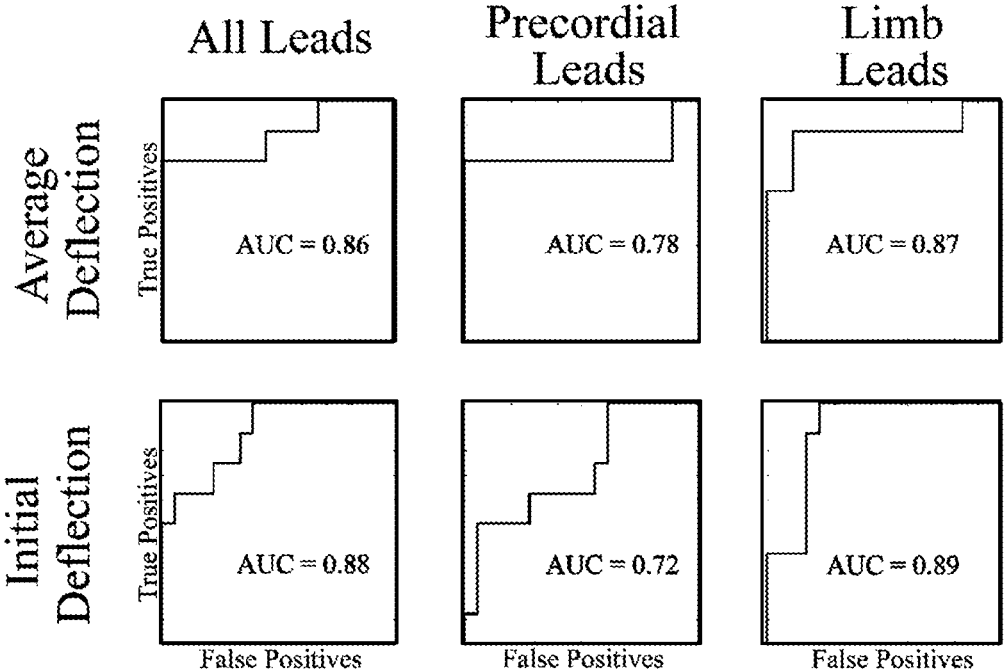
FIG. 9 is a series of graphs indicating receiver operator curves used to assess the performance of each depolarization rate calculation as a predictive measurement, according to an embodiment.

FIG. 9 depicts receiver operator curves (ROCs) used to assess the performance of each depolarization rate calculation as a predictive measurement. The ROCs were generated using both the initial depolarization and average depolarization when calculated as an average of all 12 leads, the precordial, or limb leads.

The embodiments of the present disclosure can generate a signal averaged waveform of a standard 12-Lead ECG of a patient to determine if a VT signal is endocardial or Differences in the rate of change of depolarization were compared between epicardial and endocardial VTs. Data were first compared by averaging the absolute value of the rate of change across all 12 leads within a patient. This was done for both the initial depolarization and the average depolarization. It was found that for both calculated rates of depolarization, the epicardial depolarization (average: $6.3\pm3.1$; initial $4.6\pm2.2$) was slower than that of the endocardial depolarization (average: $11.4\pm3.7$; initial $9.9\pm4.8$). This was found to be statistically significant in both the initial 30 milliseconds (p=0.0299) and for the average depolarization (p=0.0353).

Comparisons using different lead groups were done including those in the limb plane and precordial plane. Those in the limb plane were calculated by averaging the absolute value of the depolarization rate in leads I, II, II, aVF, aVL, and aVF. As was found when averaging all 12 leads, epicardial depolarization rate (average: $4.8\pm3.5$; initial $3.2\pm1.7$) was found to be slower than endocardial (average: $97\pm4.4$; initial $8.4\pm5.4$). This finding was also found to be statistically significant in both the initial 30 milliseconds (p=0.0246) and for the average depolarization (p=0.0001). The purpose of calculating within this subset of leads is to obtain a rate of depolarization from the perspective of the long axis of the heart.

The average depolarization rates for the precordial leads were averaged by using leads V1-V6. The purpose of averaging within this lead subset was to obtain an average rate of depolarization from the perspective of the short axis of the heart. Remaining consistent with the previous two calculations, the mean rate of depolarization was lower in epicardial (average: 8.5±6.0; initial 6.2±3.2) when compared to endocardial (average: 13.2±8.5; initial 11.3±7.8), however, this result was not statistically significant.

Finally, receiver operator curves were generated by varying the threshold cutoffs at which epicardial VTs were predicted (FIG. 4). When comparing the limb leads and precordial leads as predictors of epicardial VT, the limb leads were a better predictor. When the limb leads or all 12 leads were averaged, the AUC for all predictors were in a range of 0.86-0.89. In general, using the rate of change of the average depolarization was slightly higher than using only the initial depolarization. In general, less predictive power is provided when the rate of depolarization change was used from only the precordial leads (AUC of 0.72 and 0.78 for the initial rate of change and average rate of change respectively).

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

In embodiments, the various components of system 100 can be integrated into a single unit, or can be physically separated while remaining in electrical or communicative contact as discussed herein. System 100 and components or subsystems can include computing devices, microprocessors, modules and other computer or computing devices, which can be any programmable device that accepts digital data as input, is configured to process the input according to instructions or algorithms, and provides results as outputs. In one embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In one embodiment, volatile memory can include random access memory (RAM), dynamic random access memory (DRAM), or static random access memory (SRAM), for example. In one embodiment, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

In one embodiment, the system or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application specific integrated circuit (ASIC) or field programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A system for ventricular tachycardia (VT) localization comprising:

a localizer comprising a memory and a processor, the memory storing instructions that when executed by the processor cause the processor to:

receive electrocardiograph (ECG) data from an ECG device, the ECG data including electrical signals of consecutive beats of VT in a patient as recorded through each of a plurality of leads;

generate a signal averaged waveform for each lead of the plurality of leads from the ECG data, the signal averaged waveform representing a single beat;

calculate a depolarization rate for a time period for each of the signal averaged waveforms;

calculate a combined depolarization rate based on the depolarization rate of at least two of the signal averaged waveforms;

in response to the combined depolarization rate being above a threshold, generate a determination that the VT arises from an endocardial surface of the heart of the patient; and in response to the combined depolarization rate not being above the threshold, generate a determination that the VT arises from the epicardial surface of the heart of the patient; and an output device communicatively coupled to the localizer and configured to output the determination.

2. The system of claim 1, wherein the ECG data includes at least 10 consecutive beats of VT in the patient.

3. The system of claim 1, wherein the time period is the initial 30 ms of depolarization.

4. The system of claim 1, wherein the time period is a maximum deflection period extending from the beginning of depolarization to the time of maximum deflection from baseline.

5. The system of claim 1, wherein the threshold is 6 mV/s.

6. The system of claim 1, wherein the plurality of leads includes limb leads and the combined depolarization rate is calculated based on the depolarization rate of the signal averaged waveform of a I lead, a II lead, a III lead, an aVR lead, an aVL lead, and aVF lead.

7. The system of claim 1, wherein the plurality of leads includes precordial leads and the combined depolarization rate is calculated based on the depolarization rate of the signal averaged waveform of each of a V1 lead, a V2 lead, a V3 lead, a V4 lead, and a V5 lead.

8. The system of claim 1 wherein the ECG device is as 12-lead ECG device and the combined depolarization rate is calculated based on the depolarization rate of each of the twelve leads.

9. The system of claim 1, wherein the output device comprises a display configured to present the determination to a user.

10. The system of claim 1, wherein the output device comprises a network interface configured to communicate the determination to an auxiliary computing device.

11. An implantable cardiac device comprising the system of claim 1.

12. A computer-implemented method for localizing ventricular tachycardia (VT) within the heart of a patient, the method comprising:

receiving a by localizer comprising a memory and a processor, electrocardiograph (ECG) data from an ECG device, the ECG data including electrical signals of consecutive beats of VT in the patient as recorded through each of a plurality of leads;

generating a signal averaged waveform for each lead of the plurality of leads from the ECG data, the signal averaged waveform representing a single beat;

calculating a depolarization rate for a time period for each of the signal averaged waveforms;

calculating a combined depolarization rate based on the depolarization rate of at least two of the signal averaged waveforms;

in response to the combined depolarization rate being above a threshold, generating a determination that the VT arises from an endocardial surface of the heart of the patient; and in response to the combined depolarization rate not being above the threshold, generating a determination that the VT arises from the epicardial surface of the heart of the patient.

13. The method of claim 12, wherein the ECG data includes at least 10 consecutive beats of VT in the patient.

14. The method of claim 12, wherein the time period is the initial 30 ms of depolarization.

15. The method of claim 12, wherein the time period is a maximum deflection period extending from the beginning of depolarization to the time of maximum deflection from baseline.

16. The method of claim 12, wherein the threshold is 6 mV/s.

17. The method of claim 12, wherein the plurality of leads includes limb leads and the combined depolarization rate is calculated based on the depolarization rate of the signal averaged waveform of a I lead, a II lead, a III lead, an aVR lead, an aVL lead, and aVF lead.

18. The system of claim 12, wherein the plurality of leads includes precordial leads and the combined depolarization rate is calculated based on the depolarization rate of the signal averaged waveform of each of a V1 lead, a V2 lead, a V3 lead, a V4 lead, and a V5 lead.

19. The method of claim 12 wherein the ECG device is a 12-lead ECG device and the combined depolarization rate is calculated based on the depolarization rate of each of the twelve leads.

20. The method of claim 12, further comprising performing a procedure on the patient to treat epicardial VT when the determination is that the VT arises from the epicardial surface or to treat endocardial VT when the determination is that the VT arises from the endocardial surface.

* * * * *